(12) United States Patent
Steen

(10) Patent No.: US 7,331,927 B2
(45) Date of Patent: Feb. 19, 2008

(54) METHODS AND SYSTEMS FOR MEDICAL IMAGING

(75) Inventor: Erik Normann Steen, Moss (NO)

(73) Assignee: General Electric Company, Schenectady, NY (US)

( * ) Notice: Subject to any disclaimer, the term of this patent is extended or adjusted under 35 U.S.C. 154(b) by 692 days.

(21) Appl. No.: 10/695,209

(22) Filed: Oct. 28, 2003

(65) Prior Publication Data

US 2005/0090745 A1   Apr. 28, 2005

(51) Int. Cl.
*A61B 8/00* (2006.01)

(52) U.S. Cl. ...................... 600/447; 128/916

(58) Field of Classification Search ........ 600/443–447, 600/454–456, 458; 128/916; 73/625–626
See application file for complete search history.

(56) References Cited

U.S. PATENT DOCUMENTS

| | | | |
|---|---|---|---|
| 5,993,390 A | * | 11/1999 | Savord et al. ............. 600/437 |
| 6,228,028 B1 | | 5/2001 | Klein et al. |
| 6,310,828 B1 | | 10/2001 | Mumm et al. |
| 6,398,731 B1 | | 6/2002 | Mumm et al. |
| 6,544,175 B1 | | 4/2003 | Newman |
| 6,572,549 B1 | | 6/2003 | Jong et al. |
| 6,582,372 B2 | | 6/2003 | Poland |
| 6,589,177 B1 | | 7/2003 | Detmer et al. |

\* cited by examiner

*Primary Examiner*—Francis J. Jaworski
(74) *Attorney, Agent, or Firm*—The Small Patent Law Group LLP; Dean D. Small

(57) ABSTRACT

A medical imaging system includes an image sensor that receives imaging signals from a region of interest, a memory coupled to the image sensor, and a processor coupled to the memory. The memory stores image data derived from the imaging signals for first and second sub-regions of the region of interest acquired during a first and second occurrence of a physiologic cycle. The processor initiates display of the first image data while the second image data is being acquired and initiates display of the first image data joined with the second image data after the second image data is acquired.

24 Claims, 4 Drawing Sheets

METHODS AND SYSTEMS FOR MEDICAL IMAGING

BACKGROUND OF THE INVENTION

This invention relates generally to medical imaging systems. More specifically, this invention relates to real time display of complex medical images obtained with a medical imaging system.

Doctors and technicians commonly employ medical imaging systems to obtain, display, and study images for diagnostic purposes. In ultrasound imaging systems, for example, a doctor may obtain heart images in an attempt to learn whether the heart functions properly. In recent years, these imaging systems have become very powerful, and often include the capability to display a looping series of ultrasound images.

The looping series of images appears to the viewer as a short repeating movie or video of the internal structures imaged during a series of ultrasound firings. In a cardiology examination, for example, the imaging system may capture ultrasound images of the heart. In the past, however, the time and space presentation of such images has been limited because of the time-consuming processing (including firing ultrasound beams, receiving the beams, and beamforming) associated with generating the images.

While it would be beneficial in many instances for a doctor to view a rapid or real-time image sequence of a three dimension region over a significant section of anatomy, such display has typically not been possible. Generally, as the size or resolution of the three dimensional volume showing the region is increased, the slower the ultrasound system obtained and displayed the three dimensional volume. Conversely, as the size or resolution of the three dimensional volume was decreased, the faster the ultrasound system could obtain and display the three dimensional volume.

However, at the point where the ultrasound system could acquire and display three dimensional volumes in real-time, the anatomical region that was imaged was too small in size or resolution to be diagnostically useful. Thus, prior ultrasound systems were limited to slowly displaying large regions or high resolutions, or quickly displaying small regions (without sufficient content) or low resolutions quickly. In other words, in three dimensional imaging in particular, there was a limit to how large of an image could be acquired and displayed in real-time with sufficient resolution in time and space while presenting clinically relevant data.

More recently, ultrasound systems have become available that acquire and display three dimensional ultrasound images assembled from multiple lines of ultrasound data. Due to both system limitations and physical limitations related to the speed of sound, only a limited number of ultrasound lines can be acquired simultaneously. These lines must be closely spaced so that the spatial resolution of the volume is sufficient for clinical use. With these restrictions it is only possible to acquire a limited volume with any rapidity.

One technique for compensating for the physical limitations in acquiring ultrasound data, was to acquire several sequences (cineloops) of sub-volumes. The sub volumes could be combined together in order to create a larger image which could be displayed after the acquisition of all the sub-volumes was finished (see for example, U.S. Pat. No. 6,544,175 to Richard M. Newman). Thus, ultrasound data acquired in different heart cycles (but at the same time relative to the heart cycle) were displayed together. However, this technique suffers from a significant drawback in that the display of the full image is done only after the acquisition of all of the sub-volumes. During acquisition; only data from the presently acquired subregion is displayed. Thus, the doctor or technician performing the acquisition only obtains limited diagnostic information during acquisition.

Therefore, there is a need for systems and methods that address the difficulties set forth above and others previously experienced.

BRIEF DESCRIPTION OF THE INVENTION

In one embodiment, a medical imaging system includes an image sensor that receives imaging signals from a region of interest, a memory coupled to the image sensor, and a processor coupled to the memory. The memory stores image data derived from the imaging signals for a first sub-region of the region of interest acquired during a first occurrence of a physiologic cycle. The memory also stores image data for a second sub-region of the region of interest acquired during a second occurrence of the physiologic cycle. The processor initiates display of the first image data while the second image data is being acquired. The processor also initiates display of the first image data joined with the second image data after the second image data is acquired. The clinical utility of the methods and systems may be enhanced by repeatedly displaying the complete region of interest while acquiring and replacing old data within the sub-regions.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the operating principles of the image acquisition and display systems and methods. In the figures, like reference numerals designate corresponding parts throughout the different views.

DETAILED DESCRIPTION OF THE INVENTION

Figure 1:
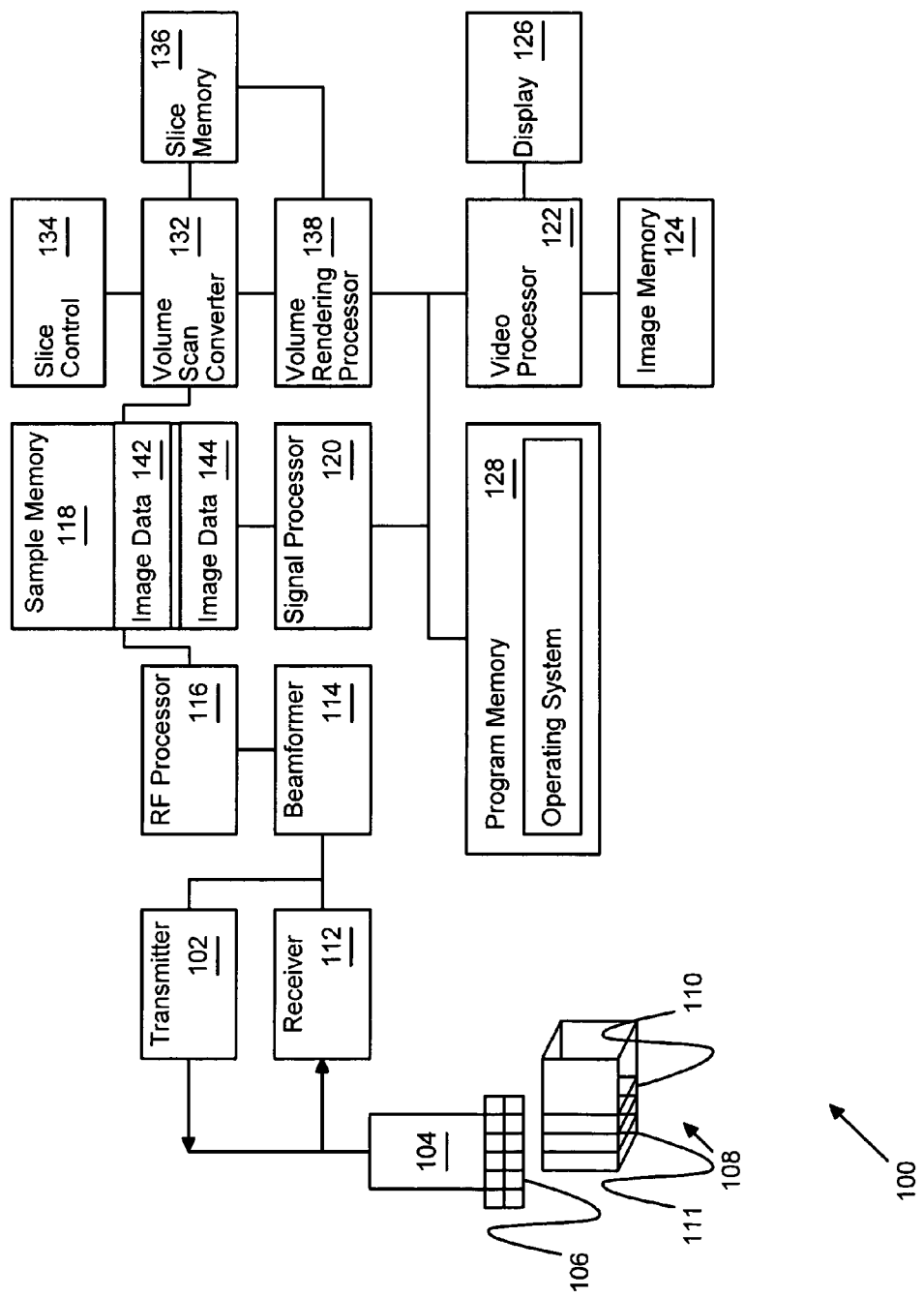
FIG. 1 illustrates an ultrasound imaging system suitable for use with the image acquisition and display techniques and systems discussed below.

Before turning in detail to the image display and acquisition techniques and systems, an exemplary ultrasound imaging system suitable for using the techniques is summarized with reference to FIG. 1. The invention is not limited to use with ultrasound systems, however, and may instead find use in a wide variety of imaging systems in which physiologic structure is displayed, including X-ray systems, fluoroscopic systems, and so forth.

FIG. 1 illustrates a diagram of the functional blocks of an ultrasound system 100. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, and so forth). Similarly, the programs may be separate stand alone programs or routines in a single program, may be incorporated as functions in an operating system, may be subroutines or functions in an installed imaging software package, and so forth.

The ultrasound system 100 includes a transmitter 102 which drives an ultrasound probe 104. The ultrasound probe 104 includes an array of transducer elements 106 that emit pulsed ultrasonic signals into a region of interest 108 (e.g., a patient's chest). In some examinations, the probe 104 may be moved over the region of interest 108, or the beamformer 114 may steer ultrasound firings, in order to acquire image information in sub-volumes or scan planes 110, 111 of the region of interest 108.

The transducer array 106 may conform to one of many geometries, as examples, a 1D, 1.5D, 1.75D, or 2D probe. The probe 104 is one example of an image sensor that may be used to acquire imaging signals from the region of interest 108. Other examples of image sensors include solid state X-ray detectors, image intensifier tubes, and the like. Structures in the region of interest 108 (e.g., a heart, blood cells, muscular tissue, and the like) back-scatter the ultrasonic signals. The resultant echoes return to the transducer array 106.

In response, the transducer array 106 generates electrical signals that the receiver 112 receives and forwards to the beamformer 114. The beamformer 114 processes the signals for steering, focusing, amplification, and the like. The RF signal passes through the RF processor 116 or a complex demodulator (not shown) that demodulates the RF signal to form in-phase and quadrature (I/Q) data pairs representative of the echo signals, or multiple individual values obtained from amplitude detection circuitry. The RF or I/Q signal data may then be routed directly to the sample memory 118 for temporary storage as 2D or 3D image data 142 for a first sub-region and 2D or 3D image data 144 for a second sub-region of the region of interest 108.

The ultrasound system 100 also includes a signal processor 120 to process the acquired ultrasound image data and prepare the ultrasound image data (e.g., as graphical images) for display. To that end, the signal processor 120 may provide the ultrasound information to the video processor 122. The video processor 122 stores frame data in the image memory 124, and outputs the video signals that drive the display 126. The display 126 may be, as examples, a CRT or LCD monitor, hardcopy device, or the like.

The signal processor 120 executes instructions out of the program memory 128. The program memory 128 stores, as examples, an operating system for the ultrasound system 100, image processing programs, image acquisition or scheduling programs, image display programs, and so forth.

In general, the signal processor 120 performs any selected processing operation available on the acquired ultrasound information chosen from the configured ultrasound modalities present in the imaging system 100. The signal processor 120 may process in real-time acquired ultrasound information during a scanning session as the echo signals are received. Additionally or alternatively, the ultrasound information may be stored in the sample memory 118 during a scanning session and processed and displayed later after the examination is complete. As will be explained in more detail below, the signal processor 120 may coordinate display of image sub-regions to provide real-time or pseudo real-time display of large regions of interest at high resolutions.

In general, the ultrasound system 100 may acquire ultrasound image data at a selected frame rate (e.g., 5-50 2D or 3D images per second) and display the derived 2D or 3D images at the same or different frame rate on the display 126. The memories shown in FIG. 1 may store processed frames that are not scheduled for immediate display. In one embodiment, as will be described in more detail below, the ultrasound system 100 acquires the image sub-regions in accordance with triggering information, and associates the sub-regions with time stamps so that the ultrasound system 100 may present looping image sequences on the display 126. The triggering information may be electrocardiogram (ECG) information, such as the QRS syndrome, systole or diastole conditions, and so forth.

The sub-regions may be two dimensional (2D) or three dimensional (3D) images or volumes acquired from the entire region of interest 108. The sub-regions need not be contiguous within the region of interest 108. To that end, the probe 104 may be used in conjunction with techniques including 3D scanning, real-time 3D imaging, volume scanning, 2D scanning with transducers having positioning sensors, freehand scanning using a voxel correlation technique, 2D or matrix array transducers and the like, with the beamformer 114 steering the ultrasound beams to acquire image data for the desired sub-regions over the entire region of interest 108.

When the probe 104 moves, or the beamformer 114 steers firings, along a linear or arcuate path, the probe 104 scans the region of interest 108. At each linear or arcuate position, the probe 104 fires an ultrasound beam into the region of interest 108. The returning echoes are collected to cover a selected thickness, for example, by collecting adjacent scan planes. The scan planes are stored in the memory 118, and then passed to a volume scan converter 132. In some embodiments, the probe 104 may obtain lines instead of the scan planes, and the memory 118 may store lines obtained by the probe 104 rather than the scan planes or sub-volumes 110, 111.

The volume scan converter 132 receives a volume thickness setting from a control input 134 that an operator adjusts to choose the thickness of a volume to be acquired from the scan planes. The volume scan converter 132 assembles volume data from multiple adjacent scan planes. The number of adjacent scan planes that form each volume is dependent upon the thickness selected by the slice thickness control input 134. The volume data may be stored in the slice memory 136 for access by the volume rendering processor 138. The volume rendering processor 138 performs volume rendering upon the volume data. The output of the volume rendering processor 138 passes to the video processor 122 and display 126. In one mode of operation, the ultrasound system 100 displays sequences of images captured by the probe 104, for example as cine-loops, using image data obtained during two or more different physiologic cycles (e.g., heart cycles or respiratory cycles) to build an image that displays in real-time an extensive region of interest with a resolution that provides a clinically useful image display.

Figure 2:
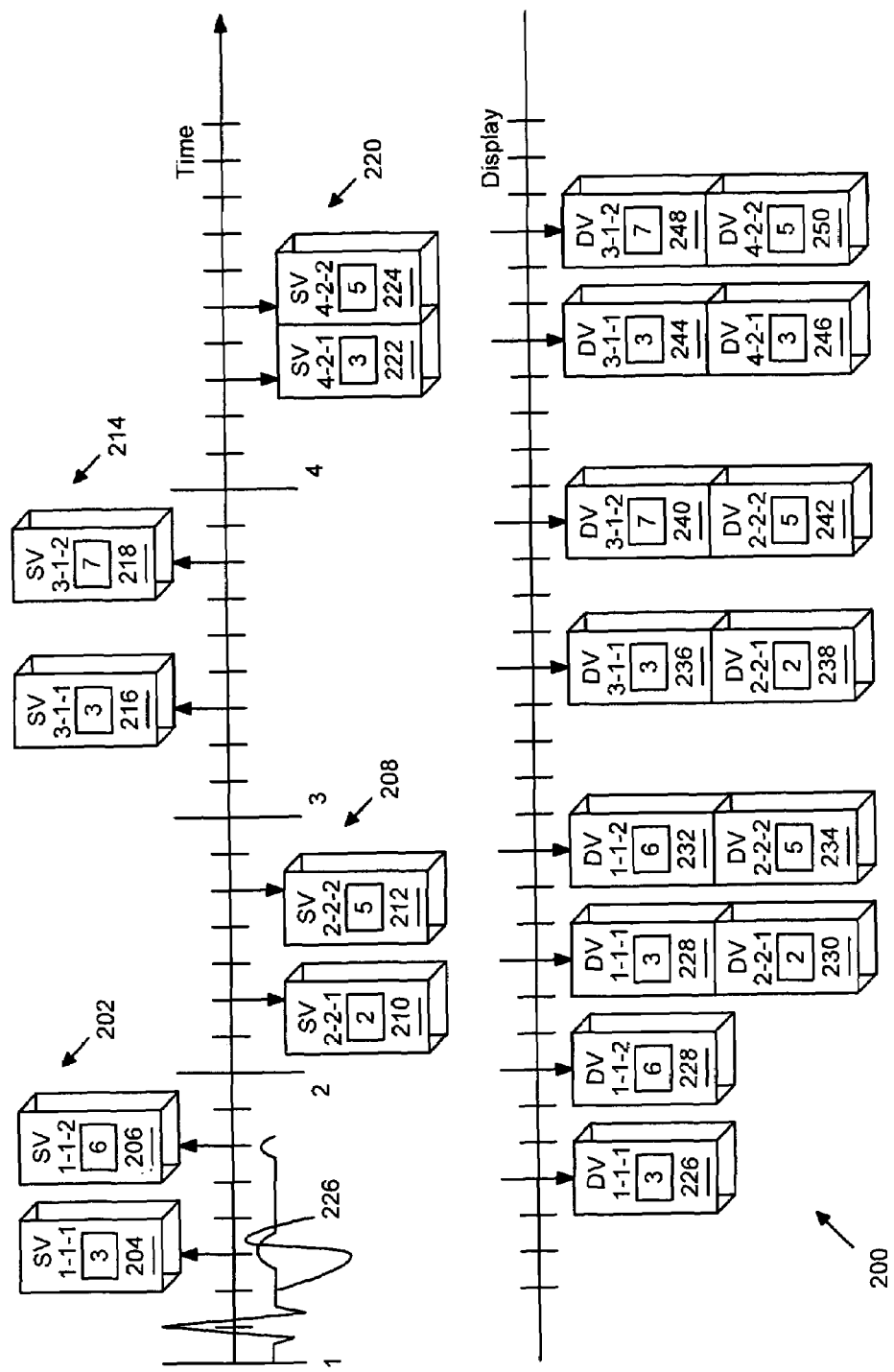
FIG. 2 shows a timing diagram of image data acquisition and display for first and second sub-regions of a region of interest.

Turning next to FIG. 2, that figure depicts a timing diagram 200 of image data acquisition and display for first and second sub-regions of a region of interest. As shown in FIG. 2, the ultrasound imaging system 100 over time acquires the first series 202 of volume data 204, 206 of a first sub-region 110 in the region of interest 108. The imaging system 100 similarly acquires the second series 208 of volume data 210, 212 of a second sub-region 111 in the region of interest 108.

Over time, the imaging system 100 supplements the first series 202 with a third series 214 of additional volume image data 216, 218 of the first sub-region 110. The imaging system 100 supplements the second series 208 with a fourth series 220 of additional volume image data 222, 224 of the second sub-region 111. The imaging system 100 may supplement acquired image data by replacing the old image data, or by storing the newly acquired image data in memory in addition to already existing image data. There may be more or fewer than two sets of volume image data acquired during a pre-selected span of time (e.g., a cardiac cycle), as well as more or fewer than two sub-regions. Thus, for example, the imaging system 100 may acquire 5-20 new sets of volume image data per second, and display the volume images as explained below.

The imaging system 100 may obtain the volume images according to any desired imaging schedule. In one embodiment, the volume images are obtained during physiologic event cycles (e.g., a heartbeat). Associated physiologic event triggers indicate to the imaging system 100 that a physiologic cycle is starting or that a physiologic event of interest is going to occur. Thus, for example, the event trigger may be based on the ECG signal 226. More specifically, the event trigger may be a portion of the ECG signal 226 that indicates the QRS syndrome, the expected end-systole or end-diastole conditions, and the like.

In FIG. 2, the volume image data is labeled according to the cardiac cycle in which they are obtained, the sub-region for which they contain image data, and the image number within the cardiac cycle (X-Y-Z). Thus, for example, the volume image data 206 is labeled SV 1-1-2 to indicate that it is Sample Volume image data from the first cardiac cycle for the first sub-region 110, and is the second volume image data obtained for that sub-region during the first cardiac cycle. Similarly, the volume image data 222 is labeled SV 4-2-1 to indicate that it is Sample Volume image data from the fourth cardiac cycle for the second sub-region 111, and is the first volume image obtained for that sub-region during the fourth cardiac cycle. The SV (X-Y-Z) notation is primarily used for reference below and does not necessarily represent data that is stored with the volume image data.

In one embodiment, however, the imaging system 100 associates the volume image data with a temporal indicator. As examples, the temporal indicator may be a time stamp indicating a number of milliseconds from a given event trigger or from a fixed time reference. Note that the event trigger may vary between physiologic cycles. For example, the QRS syndrome may occur at different times in different cardiac cycles. FIG. 2 shows the timestamps associated with the volume image data as a number enclosed in a square, and superimposed on the volume image data. Thus, for example, the volume image data 206 has the timestamp 6, while the volume image data 222 has the timestamp 3, measured from the onset of a trigger condition in each cardiac cycle.

The timing diagram in FIG. 2 also shows how the imaging system 100 displays the volume image data that has been acquired, as new volume image data continues to be acquired. The volume image data that are displayed are labeled Display Volume (DV) (X-Y-Z) to show the correspondence to the sampled volume (SV) image data.

Initially, the current cardiac cycle is cycle 1 and the imaging system 100 acquires the volume image data 204. While acquiring the volume image data 206, the imaging system 100 displays the volume image data 204 as the display volume 226. The display volume 226 is derived from the volume image data 204, for example, by optionally performing any 2D or 3D rendering, edge detection, or other image processing operations to the volume image data 204. Similarly, when the imaging system 100 acquires the volume image data 206 (an image of the same sub-region 110, but later in time), the imaging system displays the volume image data 206 as the display volume 228, while switching to and acquiring the volume image data 210 for the second sub-region 111. Generally, the imaging system 100 regularly switches between two or more sub-regions for image acquisition, while displaying image data previously obtained for the sub-regions not currently being imaged.

During cardiac cycle 2, once the imaging system 100 acquires the volume image data 210, the imaging system 100 may join together image volumes obtained from the first sub-region 110 and the second sub-region 111 on the display. To that end, in cineloop fashion, the imaging system 100 returns to the first volume image data 204 for display. Even though the first volume image data 204 was obtained in a prior cardiac cycle, the imaging system repeats the display of the volume image data 204, joined with a selected image volume from the second, current, cardiac cycle.

In one implementation, the imaging system 100 selects volume image data that is closest in time (as determined by comparing time stamps) for joining together on the display. Thus, as shown in FIG. 2, the imaging system 100 joins volume image data 204 (timestamp 3) with volume image data 210 (timestamp 2) to create an image on the display that includes the display volume 228 joined with the display volume 230. In general, display volumes are joined together by presenting them together on a display screen at selected locations. The display volumes need not be displayed overlapping or side-by-side, but may be non-contiguous portions of the region of interest 108 and displayed as such.

Continuing with the example shown in FIG. 2, the imaging system 100 presents the display volumes 228 and 230 while the imaging system 100 continues to acquire new volume image data. More specifically, the imaging system 100 presents the display volumes 228 and 230 while the imaging system 100 acquires the volume image data 212. Once the volume image data 212 is available, and the imaging system 100 moves on to display the next volume image data 206 in the series 202, the imaging system may then determine that the volume image data 212 is closest in time to the volume image data 206.

As a result, while the imaging system 100 acquires additional volume image data, the imaging system 100 presents the display volume 232 (derived from the volume image data 206) joined with the display volume 234 (derived from the volume image data 212).

Moving forward, the imaging system 100 supplements the first series 202 with the third series 214 of volume image data acquired in cardiac cycle 3. The imaging system 100 may therefore turn to the third series 214 of volume image data for display, rather than the first series 202 of volume image data acquired during the first cardiac cycle. In other words, the imaging system 100 may use the most recently acquired image data for a sub-region for display, even though the most recently acquired image data may not be from the current physiologic cycle.

The imaging system 100 uses the newly acquired volume image data 216 for display, replacing the older volume image data 204. Thus, as shown in FIG. 2, the imaging system 100 presents the display volume 236 (derived from the volume image data 216) joined with the display volume 238. The display volume 238 is derived from the volume image data (for the second sub-region) closest in time to the volume image data 216 (time stamp 3). In this case, the closest volume image data is the volume image data 210 (time stamp 2) obtained during the second cardiac cycle. Similarly, after the volume image data 218 is obtained, the imaging system 100 presents the display volume 240 (derived from the volume image data 218) joined with the display volume 242 (derived from the volume image data 212). Again, the volume image data 212 is the volume image for the second sub-region that is closest in time to the volume image data 218.

The display process occurs as the imaging system 100 continues to obtain new volume image data. The imaging system 100 next supplements the second series 208 with the fourth series 220 of volume image data acquired in cardiac cycle 4. The imaging system 100 may then replace the display of volume image data 210 and 212 with volume image data 222 and 224. Thus, as examples, the imaging system 100 presents the display volume 244 (derived from the volume image data 216) joined with the display volume 246 (derived from the volume image data 222), and presents the display volume 248 (derived from the volume image data 218) joined with the display volume 250 (derived from the volume image data 224).

The imaging system 100 may continue to supplement the image data at a pre-selected rate for a specified time. When the imaging system 100 no longer acquires new image data, the imaging system 100 may nevertheless continue to display in single loop or cineloop fashion images derived from the image data that it already has acquired, as described above.

Figure 3:
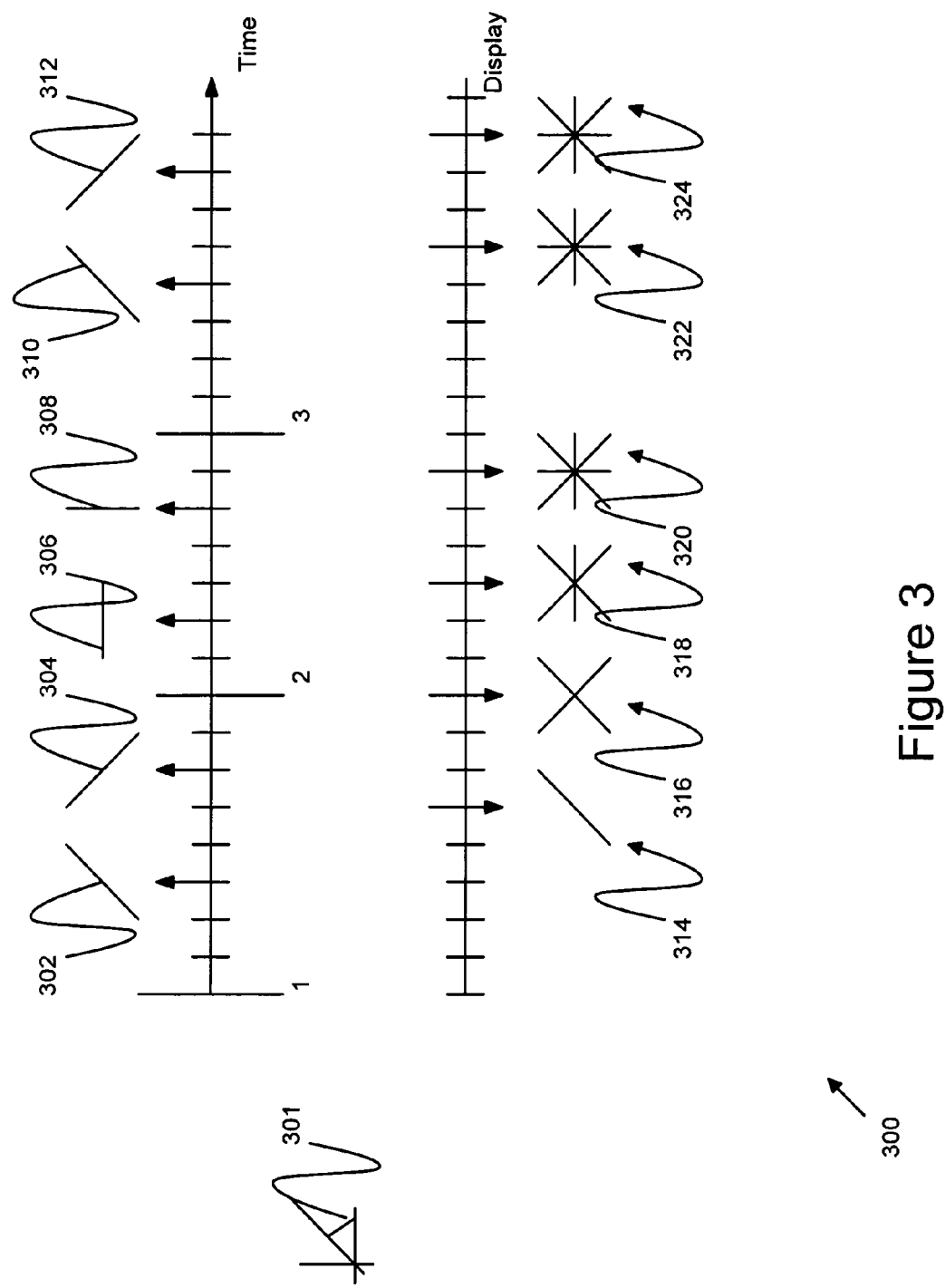
FIG. 3 shows a second timing diagram of image data acquisition and display.

With regard next to FIG. 3, that figure shows a timing diagram 300 for a second technique of image data acquisition and display for first and second sub-regions of a region of interest. As shown in FIG. 3, the ultrasound imaging system 100 over time acquires, at various angles 301 (relative, for example, to the image sensor 104 azimuth or elevation directions), the scan planes 302, 304, 306, 308, 310, and 312.

The scan planes 302 and 304 are obtained during a first cardiac cycle to provide image data over that cardiac cycle for a first sub-region of interest. Similarly, the scan planes 306 and 308 are obtained during a second cardiac cycle to provide image data over that cardiac cycle for a second sub-region of interest. In a manner similar to that described above with regard to FIG. 2, the imaging system 100 alternates between sub-regions during image acquisition and, for example, supplements the scan planes 302 and 304 with newly acquired scan plane image data 310 and 312.

As shown along the display timeline in FIG. 3, the imaging system displays the first image 314 using the scan plane 302. When the scan plane 304 is obtained, the imaging system 100 presents (as it proceeds to acquire additional scan planes) the second image 316 that includes both scan planes 302-304. As shown in FIG. 3, the scan planes intersect, but the scan planes may in fact be obtained (due to beamformer 114 steering) from any desired location or angle 301 within the region of interest.

The displayed image thus begins to form a larger overall image as additional scan planes are obtained. Continuing forward, the imaging system 100 acquires the scan plane 306, and, as the imaging system 100 obtains the scan plane 308, it displays a new image 318 that includes the scan planes 302-306. The imaging system 100, after acquiring the scan plane 308, displays a new image 320 that includes the scan planes 302-308.

At the same time, the imaging system 100 acquires the scan plane 310 to supplement the scan planes obtained during the first cardiac cycle. Thus, when the imaging system 100 displays the image 322, the imaging system may instead use scan plane 310 with the scan planes 304, 306, and 308. In other words, the scan plane 302 has be replaced with the newly obtained scan plane 310. In a similar fashion, the imaging system 100 may next replace the scan plane 304 with a newly acquired scan plane 312. The resulting image 324 thus includes the scan planes 310, 312, 306, and 308. In a similar manner, the imaging system 100 may continue to supplement older image data, and present an overall image constructed from the most recent scan planes (which need not be acquired in the most recent physiologic cycle).

Figure 4:
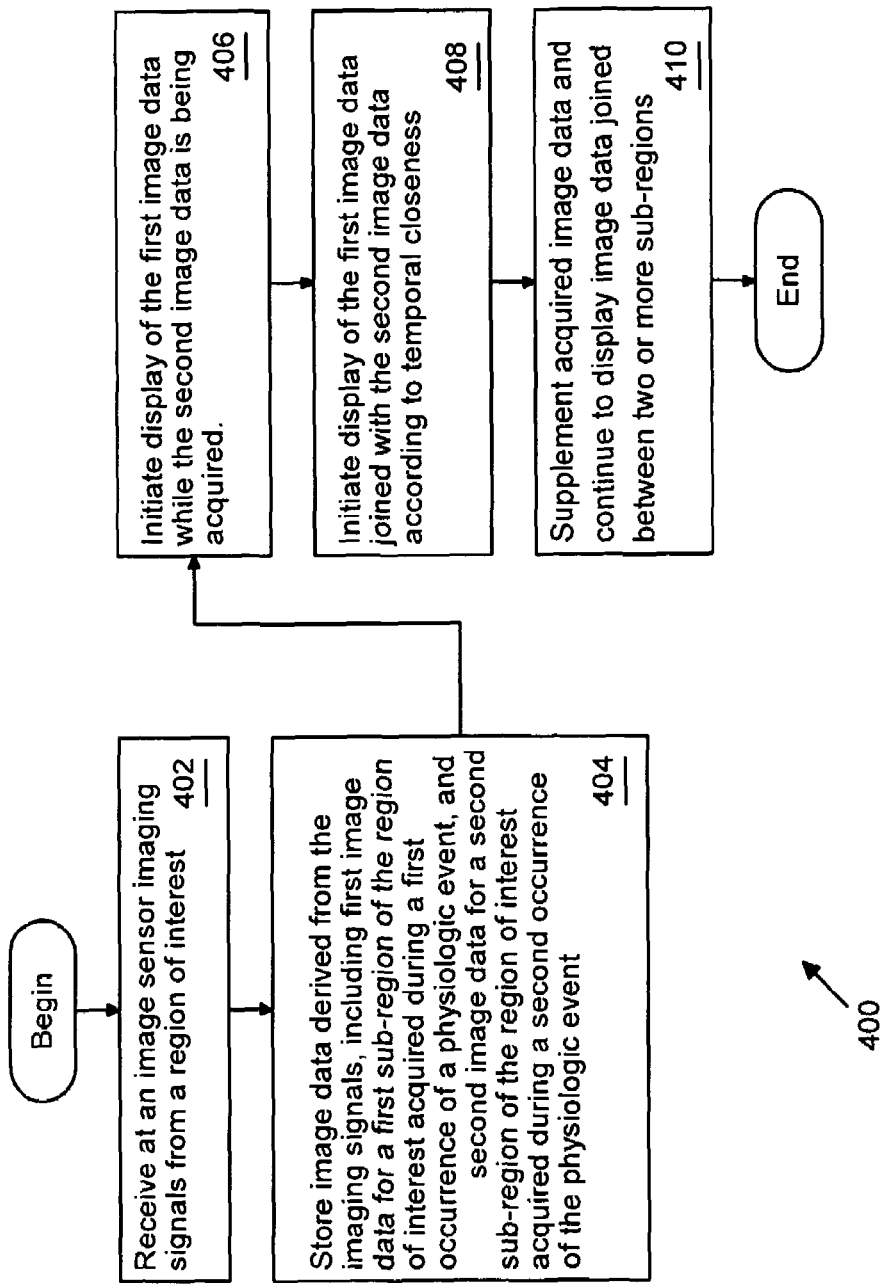
FIG. 4 shows the steps taken by the imaging system shown in FIG. 1 to acquire and display sub-regions of a region of interest.

Turning next to FIG. 4, that figures summarizes the steps 400 taken by the imaging system 100 to acquire and display sub-regions of a region of interest. The imaging system 100 first receives, at an image sensor 104, imaging signals from a region of interest 108 (Step 402). The imaging system 100 then stores image data derived from the imaging signals (Step 404). The image data typically includes image data 204, 206 for a first sub-region 110 of the region of interest 108 acquired during a first occurrence of a physiologic event, as well as image data 210, 212 for a second sub-region 111 of the region of interest 108 acquired during a second occurrence of the physiologic event.

The imaging system 100 initiates display of image data while additional image data is being acquired (Step 406). In doing so, the imaging system 100 initiates display (e.g., by commanding a graphics processor to render and display an image) of the image data 204, 206 joined with the image data 210, 212 after the additional image data is acquired, and as more image data is being acquired (Step 408). Furthermore, the imaging system 100 may continue to supplement already acquired image data, and to construct images that include two more sub-regions joined together (selected, for example, according to temporal closeness) (Step 410).

Thus, the ultrasound system 100 provides an image acquisition and display system that improves upon prior image acquisition and display techniques. To summarize, the imaging system 100 allows the doctor or technician to visualize the full 4D dataset for a region of interest 108 (i.e., time and a 3D volume) while the imaging system 100 continues to acquire sub-regions of the full dataset. As a result, the doctor or technician can then see in real time the entire dataset while it is being acquired. When the last sub-region in the sequence has been acquired, the imaging system 100 can continue to acquire and replace the oldest dataset with new data.

The imaging system 100 thereby provides a pseudo real time imaging mode where data acquired in real time is displayed together with data acquired in previous physiologic (e.g., heart) cycles. While an ECG signal may be used to detect the heart cycles and provide an event trigger, other sources of event triggers may also be used. Note also that while the imaging system 100 is particularly suited for 3D imaging, the techniques described are more general and may be used to combine differently oriented 2D images from different physiologic cycles into one display, as shown in FIG. 3.

While various embodiments of the invention have been described, it will be apparent to those of ordinary skill in the art that many more embodiments and implementations are possible that are within the scope of this invention. The foregoing description has been presented for the purposes of illustration and explanation. It is not intended to be exhaustive or to limit the invention to the precise form disclosed.

While the invention has been described in terms of various specific embodiments, those skilled in the art will recognize that the invention can be practiced with modification within the spirit and scope of the claims.

What is claimed is:

1. A medical imaging system comprising:
   an image sensor receiving imaging signals from a region of interest defining an image volume;
   a memory coupled to the image sensor, the memory storing image data derived from the imaging signals, where the image data comprise:

first image data for a first sub-region of the region of interest defining an image sub-volume and acquired during and synchronized to a first occurrence of a physiologic cycle;

second image data for a second sub-region of the region of interest defining an image sub-volume and acquired during and synchronized to a second occurrence of the physiologic cycle; and a processor coupled to the memory for initiating display of the first image data while the second image data is being acquired, and for initiating display of the first image data joined with the second image data after the second image data is acquired based on the physiologic synchronization to form a larger overall image encompassing the image volume while other sub-volumes are being acquired.

2. The medical imaging system of claim 1, where the first image data is supplemented with third image data for the first sub-region of the region of interest acquired during a third occurrence of the physiologic cycle.

3. The medical imaging system of claim 2, where the processor initiates display of the first image data joined with the second image data after the second image data is acquired and while the third image data is being acquired, and further initiates display of the third image data joined with the second image data after the third image data is acquired.

4. The medical imaging system of claim 3, where the second image data is supplemented with fourth image data for the second sub-region of the region of interest acquired during a fourth occurrence of the physiologic cycle.

5. The medical imaging system of claim 4, where the processor initiates display of the third image data joined with the second image data after the third image data is acquired and while the fourth image data is being acquired, and further initiates display of the third image data joined with the fourth image data after the fourth image data is acquired.

6. The medical imaging system of claim 1, where the image sensor is an ultrasound transducer array.

7. The medical imaging system of claim 1, where the image data comprises ultrasound image lines for the sub-regions.

8. The medical imaging system of claim 1, where the physiologic cycle is a heart cycle, and where the region of interest includes at least part of the heart.

9. The medical imaging system of claim 1, where the first and second imaging data are acquired based on an event trigger for the physiologic cycle.

10. The medical imaging system of claim 9, where the physiologic cycle is an ECG cycle and the event trigger is an ECG event.

11. The medical imaging system of claim 1, where the first image data is associated with a first time stamp, and is updated at least once with additional first image data associated with a second time stamp for the first sub-region during the first occurrence of the physiologic cycle.

12. The medical imaging system of claim 11, where the first and second sub-regions are non-contiguous.

13. The medical imaging system of claim 11, where the second image data is associated with a third time stamp, and is updated at least once with additional second image data associated with a fourth time stamp for the second sub-region during the second occurrence of the physiologic cycle.

14. The medical imaging system of claim 13, where the processor selects first and second image data for display based on closeness of the time stamps.

15. The medical imaging system of claim 1, where the processor repeatedly supplements the image data with additional image data and repeatedly joins and displays selected portions of the additional image data.

16. The medical imaging system of claim 1, where the processor repeatedly supplements the image data with additional image data and repeatedly joins and displays selected portions of the additional image data.

17. The medical imaging system of claim 1, where the first image data comprises a first series of first sub-region images and the second image data comprises a second series of second sub-region images.

18. A method for medical imaging, the method comprising the steps of:

receiving at an image sensor imaging signals from a region of interest defining an image volume;

storing in a memory image data derived from the imaging signals, including:

first image data for a first sub-region of the region of interest defining an image sub-volume and acquired during and synchronized to a first occurrence of a physiologic cycle; and second image data for a second sub-region of the region of interest defining an image sub-volume and acquired during and synchronized to a second occurrence of the physiologic cycle;

initiating display of the first image data while the second image data is being acquired; and initiating display of the first image data joined with the second image data after the second image data is acquired based on the physiologic synchronization and while other sub-volumes are being acquired, the first image data and second image data defining a larger image than the first image data and encompassing the image volume;

supplementing the first image data with third image data for the first sub-region of the region of interest acquired during a third occurrence of the physiologic cycle.

19. The method of claim 18, further comprising the step of supplementing the first image data with third image data for the first sub-region of the region of interest acquired during a third occurrence of the physiologic cycle.

20. The method of claim 19, where the second step of initiating comprises the step of initialing display of the first image data joined with the second image data after the second image data is acquired and while the third image data is being acquired, and further comprising the step of initiating display of the third image data joined with the second image data after the third image data is acquired.

21. The method of claim 19, where the physiologic cycle is an ECG cycle and the event trigger is an ECG event.

22. The method of claim 18, where the step of receiving comprises the step of receiving at an ultrasound transducer array.

23. The method of claim 18, where the first and second imaging data are acquired based on an event trigger for the physiologic cycle.

24. The method of claim 18, further comprising the step of repeatedly supplementing the image data with additional image data and repeatedly joining and displaying selected potions of the additional image data.

* * * * *